United States Patent
Klomp

(10) Patent No.: US 11,116,889 B2
(45) Date of Patent: Sep. 14, 2021

(54) CONTAINER FOR HOLDING A LIQUID

(71) Applicant: FRITZ RUCK OPHTHALMOLOGISCHE SYSTEME GMBH, Eschweiler (DE)

(72) Inventor: Manfred Klomp, Hulsberg (NL)

(73) Assignee: FRITZ RUCK OPHTHALMOLOGISCHE SYSTEME GMBH, Eschweiler (DE)

( * ) Notice: Subject to any disclaimer, the term of this patent is extended or adjusted under 35 U.S.C. 154(b) by 247 days.

(21) Appl. No.: 16/331,115

(22) PCT Filed: Sep. 4, 2017

(86) PCT No.: PCT/EP2017/072118
§ 371 (c)(1),
(2) Date: Mar. 6, 2019

(87) PCT Pub. No.: WO2018/046444
PCT Pub. Date: Mar. 15, 2018

(65) Prior Publication Data
US 2019/0224403 A1    Jul. 25, 2019

(30) Foreign Application Priority Data

Sep. 6, 2016  (EP) .................................... 16187309

(51) Int. Cl.
*A61M 3/02*   (2006.01)
*A61J 1/14*   (2006.01)
(Continued)

(52) U.S. Cl.
CPC .......... *A61M 3/0279* (2013.01); *A61J 1/1475* (2013.01); *A61M 3/0237* (2013.01);
(Continued)

(58) Field of Classification Search
CPC ...... A61M 3/0279; A61M 3/237; A61M 5/14; A61M 2210/0612; A61M 16/14;
(Continued)

(56) References Cited

U.S. PATENT DOCUMENTS

2003/0083640 A1   5/2003   Sadiow
2008/0065030 A1   3/2008   Angelini et al.
(Continued)

FOREIGN PATENT DOCUMENTS

WO      WO 96/37245      11/1996

OTHER PUBLICATIONS

PCT/EP2017/072118, Nov. 14, 2017, International Search Report and Written Opinion.

*Primary Examiner* — Brandy S Lee
*Assistant Examiner* — Nidah M Hussain
(74) *Attorney, Agent, or Firm* — Workman Nydegger

(57) ABSTRACT

A container for holding a liquid, in particular an infusion liquid or irrigating liquid, comprising a liquid phase containing the liquid and a gas phase, wherein, in the operating position, a liquid opening is formed in the lower region of the container and wherein the container has a gas opening. The gas opening is formed by a gas pipe which is inseparably connected to the container and has a first gas pipe end and a second gas pipe end. The first gas pipe end extends into the gas phase of the container and is provided with a closure. The second gas pipe end leads to the outside of the container.

11 Claims, 1 Drawing Sheet

(51) Int. Cl.
*A61J 1/10* (2006.01)
*A61M 5/14* (2006.01)

(52) U.S. Cl.
CPC .................. *A61J 1/10* (2013.01); *A61M 5/14* (2013.01); *A61M 2210/0612* (2013.01)

(58) Field of Classification Search
CPC ...... A61M 16/142; A61M 16/147; A61J 1/10; A61J 1/1475; A61J 1/05
USPC ........................................................ 604/257
See application file for complete search history.

(56) References Cited

U.S. PATENT DOCUMENTS

| | | | |
|---|---|---|---|
| 2010/0010466 A1* | 1/2010 | Muramatsu ........... | A61J 1/2093 604/410 |
| 2012/0041416 A1* | 2/2012 | Lal ....................... | A61M 39/22 604/506 |
| 2014/0276639 A1* | 9/2014 | Tarkeshian .......... | A61M 3/0216 604/521 |
| 2018/0344569 A1* | 12/2018 | Di Naro ................... | F26B 5/06 |

* cited by examiner

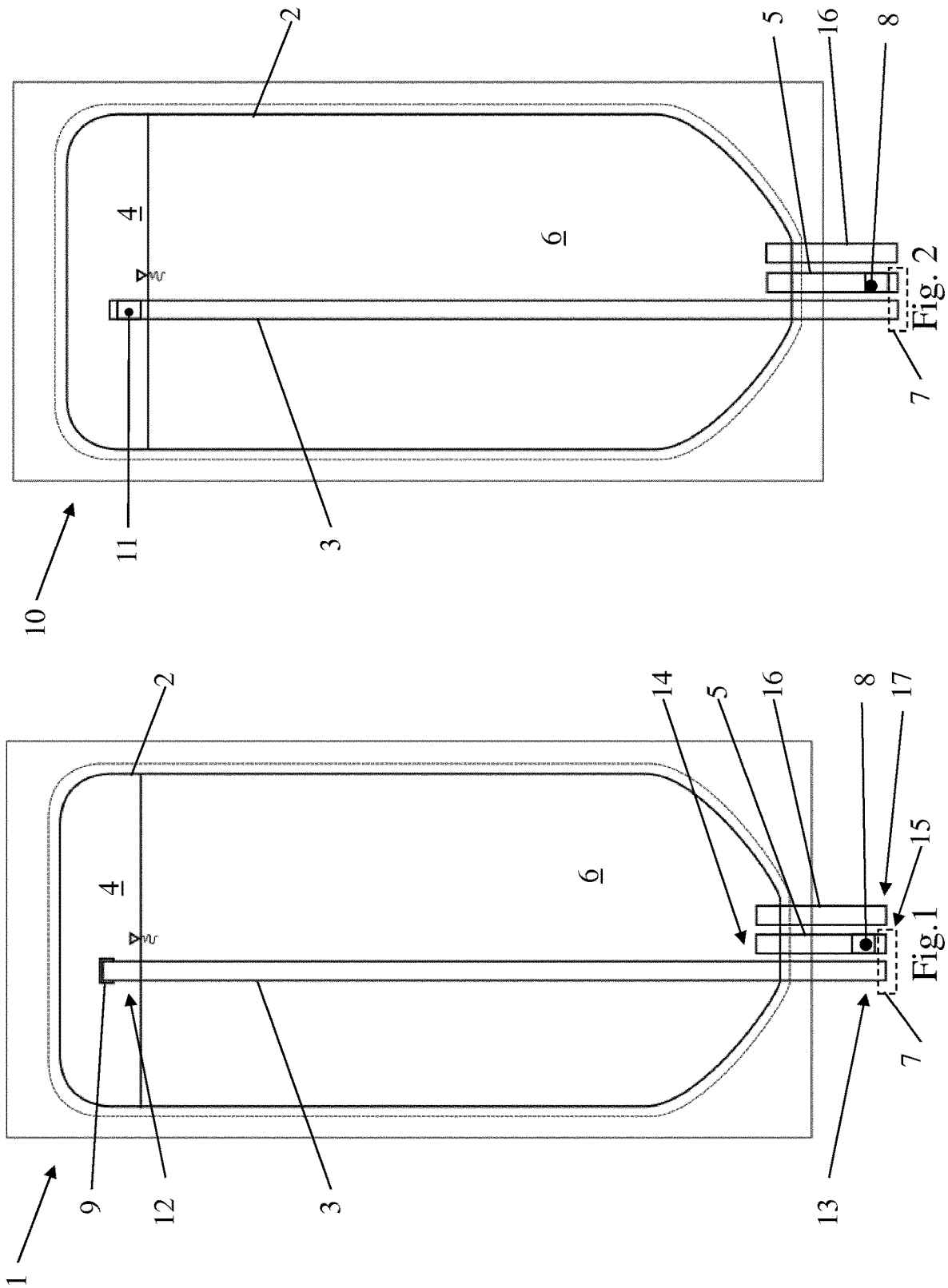

CONTAINER FOR HOLDING A LIQUID

The invention relates to a container for holding a liquid, in particular an infusion liquid or irrigating liquid, comprising a liquid phase containing the liquid and a gas phase, wherein, in the operating position, a liquid opening is formed in the lower region of the container and wherein the container has a gas opening, which gas opening is formed by a gas pipe which has a first gas pipe end and a second gas pipe end, wherein the first gas pipe end extends into the gas phase of the container and wherein the second gas pipe end leads to the outside of the container.

Containers for use in the medical field are known which include a liquid phase and a gas phase and, in the operating position, have an opening in the lower region of the container. The opening is closed with a seal for the transport of the container, which seal must be pierced by means of a mandrel for the removal of the liquid from the container. Such a container is used, for example, for infusions, wherein the removal of the liquid from the container is effected by gravity. Such a container is known, for example, from the document US 2003/0083640 A1 or WO 96/37245.

However, such containers can also be used in eye surgery devices, wherein, for removing the liquid from the container, the seal of the container must be pierced by two mandrels, with a first mandrel having such a length that, in the operating position of the container, it extends into the gas phase of the container and a second mandrel having such a length that, in the operating position of the container, it extends into the liquid phase. During a surgical procedure, gas is supplied into the container via the first mandrel by means of a controlled compressor unit connected to the first mandrel via hoses or pipes, whereby the liquid is forced out of the container by the second mandrel at a particular pressure. As a result, the discharge pressure of the liquid from the container can be controlled regardless of a fill quantity of the container with liquid and regardless of a height of a suspension point of the container.

Because of the length of the first mandrel extending into the gas phase, the disadvantage is obtained that it is difficult for a person or, respectively, a surgeon to hit the seal instantly with the long mandrel, piercing it therewith, when the container is replaced. It may also happen that, after the seal has been pierced, the side wall of the container is pierced, too, whereupon the liquid flows out uncontrollably and the container will have to be discarded. This increases not only the risk of injury to the personnel performing the operation, but also the risk of the liquid being contaminated. Furthermore, there is a high risk that, when the seal is being pierced, liquid will run into the longer pipe, which will subsequently follow gravity and come to a standstill in conduits or hoses between the container and the compressor unit or, in the very worst case, will run into the compressor unit, which, as a result, might suddenly fail. By providing water separators between the compression unit and the first mandrel, the accumulation of water in the conduits or hoses is indeed avoided, albeit only to a certain extent. Furthermore, the water separators are difficult or even impossible to clean and therefore have to be replaced regularly.

In order to evade those disadvantages, containers have been designed which are formed from an elastic plastic film and comprise two chambers. A first chamber is configured for holding a first fluid, in particular gas, and a second chamber is configured for holding a second fluid, in particular a liquid. In the operating position of the container, each of the two chambers has an opening in the lower region, wherein the second fluid is forced out of the second chamber by the supply of the first fluid into the first chamber. The first fluid and the second fluid are always separated from each other because of the design of the container. Such a container is known, for example, from the publication US 2008/0065030 A1.

It proves to be a disadvantage of the container known from the publication US 2008/0065030 A1 that the production of the container is very complex and expensive. Furthermore, it is difficult to control a pressure in the liquid phase or, respectively, pressure changes are transferred from the gas phase to the liquid phase only with delay, whereby the discharge pressure by means of which the liquid is forced through the opening out of the container, is difficult to control. However, this is indispensable for eye surgery devices, since the tissue of the eye can sustain irreparable damage during the operation both at pressures which are too low and at pressures which are too high.

It is therefore the object of the present invention to provide a container which is easy to handle and in which pressure changes in the gas phase are transferred without delay to the liquid phase.

According to the invention, the problem is solved in that the gas pipe is inseparably connected to the container, the first gas pipe end is provided with a closure, the gas pipe with the first gas pipe end extends into the gas phase from a region of the container which is lower in the operation position or from a region of the container which is upper in the operation position and the container is formed from a plastic film which has been folded and welded at the edges, with the gas pipe and the plastic film being welded to each other.

As a result, the advantage is obtained that, in the operating position of the container, the gas opening extends into the gas phase and the liquid opening extends into the liquid phase and that it can be avoided to provide mandrels as according to the prior art, by means of which a seal must be pierced when the bottle is replaced. A connection of the container to hoses or conduits occurs on an outside of the container simply by plugging the hoses or conduits into the gas opening or, respectively, the liquid opening, whereby the handling of the container is facilitated considerably. Since the gas opening extends directly into the gas phase and the liquid opening extends directly into the liquid phase and since the gas phase and the liquid phase are not separated from each other, a pressure change in the gas phase is transferred directly and without delay to the liquid phase.

The closure arranged at the end of the gas pipe serves to ensure that, during the transport of the container, that is, when it is in a position that does not correspond to its operating position, no liquid can run into the gas pipe. The closure is opened in the container only when the container is in the operating position shortly before the liquid is dispensed. Hence, it is no longer necessary to provide a liquid separator. Advantageously, the closure is formed by a safety device against breaking or a plug, wherein the plug can either be removed manually, in particular in case of elastic containers, or can be removed by pressurizing the gas opening.

Advantageously, the liquid opening and/or the second gas pipe end of the gas pipe is/are closed with a membrane, which is removed or pierced, respectively, when conduits are being connected to the liquid opening or, respectively, the gas opening. In a further embodiment variant, the liquid opening and/or the second gas pipe end of the gas pipe is/are closed with a plug made of rubber. As a result, contamination of an interior of the gas pipe or, respectively, leakage of liquid from the liquid opening during transport is prevented.

Suitably, the container is formed from an elastic plastic film which has been folded and welded at the edges. Preferably, the liquid opening is formed by a liquid pipe, with the liquid pipe and the gas pipe each being a plastic pipe. Suitably, both the gas pipe and the liquid pipe are welded to the plastic film. As a result, the advantage is obtained that the containers are very easy to manufacture in serial production with a small material expenditure and thus are inexpensive.

Further advantageous embodiments of the container according to the invention will be explained in further detail hereinbelow with reference to the figures.

FIG. 1 shows a first embodiment variant of a container according to the invention in the operating position in a schematic side view.

FIG. 2 shows a further embodiment variant of a container according to the invention in the operating position in a schematic side view.

FIG. 1 shows a first embodiment variant of the container 1 according to the invention in the operating position in a schematic side view. The container 1 is formed by an elastic plastic film, which is folded over and welded at the edges along the line 2, and comprises a liquid phase 6 and a gas phase 4. The container 1 has a gas opening formed by a gas pipe 3. The gas pipe 3 is firmly welded to the plastic film of the container 1, with a first gas pipe end 12 of the gas pipe 3 extending into the gas phase 4 in the operating position and a second gas pipe end 13 of the gas pipe 3 protruding from the container 1 in the lower region of the container 1. Furthermore, the container 1 has a liquid opening formed by a liquid pipe 5. The liquid pipe 5 is firmly welded to the plastic film of the container 1, with a first liquid pipe end 14 of the liquid pipe 5 extending into the liquid phase 6 in the operating position and a second liquid pipe end 15 of the liquid pipe 5 protruding from the container 1 in the lower region of the container 1. In addition, the container 1 has an injection opening formed by an injection pipe 16. The injection pipe 16 is firmly welded to the plastic film of the container 1 and serves for the addition of drugs into the liquid phase 6. An outwardly opening injection pipe end 17 of the injection pipe 16 is closed with a rubber plug, which is not illustrated, whereby liquid is prevented from leaking from the container 1 through the injection pipe 16. The addition of drugs into the liquid phase 6 may be effected, for example, by means of a syringe, wherein the plug is simply pierced with a needle of the syringe when drugs are being added. The second gas pipe end 13 and the second liquid pipe end 15 form a connection unit 7. As a result, the advantage is obtained that the liquid opening and the gas opening can be connected to hoses or other devices with one movement of the hand. For this purpose, the second gas pipe end 13 and the second liquid pipe end 15 suitably each have a Luer connection, which are closed by a membrane so as to avoid contamination of an interior of the gas pipe 3 and the liquid pipe 5 during a transport of the container 1. If a hose or a conduit is connected to the Luer connection, the membrane is also pierced simultaneously.

A second safety device against breaking 8 is designed in the liquid pipe 5, and a closure formed by a plug 9 is designed at the first gas pipe end 12 of the gas pipe 3. The plug 9 is designed as a plastic cap, which sits reliably at the first gas pipe end 12 of the gas pipe 3 by means of friction and due to the appropriately chosen inner diameter.

Subsequently, the use of the container 1 in an eye surgery device is described in further detail, wherein the liquid in the container 1 is formed by an irrigating liquid. Furthermore, the eye surgery device comprises a surgical handpiece, a control device and a compressor unit. The surgical handpiece is equipped with a tool for performing an eye operation and is connected to the second liquid pipe end 15 of the second liquid pipe 5 by means of a hose. The compressor unit is formed by a pump, is designed for conveying gas and is connected to the second gas pipe end 13 of the gas pipe 3 by means of a hose. By means of the control device, a liquid delivery into the eye is controllable on the surgical handpiece, wherein a pressure at which the liquid is discharged from the surgical handpiece is adjustable via the pump. Prior to the operation, the container 1 is brought into its operating position according to FIG. 1, wherein it is advantageously suspended from a hook by means of an eyelet, which is not illustrated. By applying a pressure by means of the compressor unit, the plug 9 is pressed from its closing position, which closes the first gas pipe end 12 of the gas pipe 3, into a release position, which releases the gas pipe 3. In the release position, the plug 9 can float on the surface of the liquid 6 or else can still sit on the first gas pipe end 12 in an upwardly displaced position, with openings in the peripheral wall of the plug 9 allowing the passage of gas from the gas phase 4 into the gas pipe 3. The gas phase of the container 1 is connected directly to the compressor unit for communication only as a result of this. Subsequently, the safety device against breaking 8 is opened by being bent and the liquid pipe 5 is released. The liquid flows to the surgical handpiece and is delivered to the eye under the control of the control device.

In a further embodiment variant, the first gas pipe end 12 of the gas pipe 3 extends from the region of the container 1 which is upper in the operating position into the gas phase 4 of the container 1.

FIG. 2 shows a further embodiment variant of a container 10 according to the invention in the operating position in a schematic side view. The container 10 differs from the container 1 shown in FIG. 1 in that the container 10 has a first safety device against breaking 11 instead of a plug 9, wherein the gas pipe 3 is released only as a result of said device being bent.

It may also be mentioned that a container according to the invention can be used for a variety of devices in a multitude of special fields. Such a container might be designed, for example, for dispensing paints in paint application machines, or for dispensing resins or adhesives in a coating machine for gluing materials.

The invention claimed is:

1. A container, comprising a liquid phase and a gas phase, wherein, in an operating position, a liquid opening extending into the liquid phase is formed in a lower region of the container and wherein the container includes a gas opening, which gas opening is independent of the liquid opening and is formed by a gas pipe which includes a first gas pipe end and a second gas pipe end, wherein the first gas pipe end extends into the gas phase of the container and wherein the second gas pipe end leads to an outside of the container, wherein the gas pipe is inseparably connected to the container, the first gas pipe end is provided with a closure, the gas pipe with the first gas pipe end extends into the gas phase from a region of the container which is lower in the operating position or from a region of the container which is upper in the operation position, and the container is formed from a plastic film which has been folded and welded at the edges, with the gas pipe and the plastic film being welded to each other.

2. The container according to claim 1, wherein the closure is formed by a first safety device against breaking, wherein the gas opening is released only as a result of the first safety device against breaking being bent.

3. The container according to claim 1, wherein the closure is formed by a plug which is displaceable from a closing position, which closes the gas opening, into a release position, which opens the gas opening.

4. The container according to claim 1, wherein the container has an elastic design and is made of a synthetic material.

5. The container according to claim 1, wherein the liquid opening is formed by a liquid pipe which is welded to the plastic film and has a first liquid pipe end and a second liquid pipe end, wherein the first liquid pipe end extends into the liquid phase and the second liquid pipe end leads to the outside of the container.

6. The container according to claim 5, wherein the gas pipe extends with the first gas pipe end into the gas phase from the region of the container which is lower in the operation position, and wherein the second gas pipe end and the second liquid pipe end form a connection unit.

7. The container according to claim 5, wherein the second gas pipe end comprises a Luer connection.

8. The container according to claim 5, wherein the second liquid pipe end comprises a Luer connection.

9. The container according to claim 1, wherein the liquid opening has a second safety device against breaking, wherein the liquid opening is released only as a result of the second safety device against breaking being bent.

10. An eye surgery device comprising:
a surgical handpiece,
a control device, and
a compressor unit,
wherein the eye surgery device includes the container according to claim 1, wherein the surgical handpiece is connected to the liquid opening my means of a hose, wherein the compressor unit is connected to the gas opening and is designed for controlling a gas supply into the container and wherein a liquid delivery is controllable on the surgical handpiece by means of the control device.

11. The container of claim 1, wherein the liquid is an infusion liquid or an irrigating liquid.

* * * * *